United States Patent [19]

Jolly

[11] Patent Number: 4,790,855
[45] Date of Patent: Dec. 13, 1988

[54] TOTAL ELASTIC SUPPORT MEMBER FOR USE WITH AN ORTHOPEDIC DEVICE

[76] Inventor: David F. Jolly, 2250 Holly Hall, #292, Houston, Tex. 77054

[21] Appl. No.: 31,402

[22] Filed: Mar. 27, 1987

Related U.S. Application Data

[63] Continuation-in-part of Ser. No. 903,289, Sep. 3, 1986, abandoned.

[51] Int. Cl.⁴ ................................................ A61F 2/60
[52] U.S. Cl. ..................................................... 623/32
[58] Field of Search .................................. 623/31–34; 128/165, 157, 158, 525, 133, 132 R, 82, 166; 450/107, 122, 151, 101

[56] References Cited

U.S. PATENT DOCUMENTS

| D. 244,152 | 4/1977 | Kvittingen | D24/64 |
| D. 267,434 | 12/1982 | Hubbard | D24/34 |
| D. 268,132 | 3/1983 | Hubbard | D24/34 |
| 976,550 | 11/1910 | Coddington | 128/525 |
| 2,526,360 | 10/1950 | Johnson | 450/122 |
| 4,590,932 | 5/1986 | Wilherson | 128/166 |

FOREIGN PATENT DOCUMENTS

374004 6/1907 France .......................... 128/525

Primary Examiner—Richard J. Apley
Assistant Examiner—James Prizant
Attorney, Agent, or Firm—Phillips, Moore, Lempio & Finley

[57] ABSTRACT

The present invention relates to an integral flexible elastic support member for securely gripping an orthopedic device such as a cast on a leg or for attaching an artificial leg to the residual lower limb of a human being having at least one above the knee amputation. The supporting member includes an adjustable body encircling portion having free ends which have attachment means, for detachably connecting the free ends together, and at least one integrally formed flexible cylindrical elastic sleeve portion descending downwardly from the body encircling portion to grip and provide support for at least one artificial leg. Optionally, the orthopedic member additionally includes a V-shaped adductor panel on the surface of the device to assist in positioning and with control of forces. Optionally, the supporting member also includes an opening within the adductor panel region to assist in the management of the forces. VELCRO ® hook and loop attachment means, and an elastic neoprene/nylon composite fabric are preferred materials of manufacture. Optionally, the sleeve is formed by connecting second detachable attachment means.

42 Claims, 5 Drawing Sheets

TOTAL ELASTIC SUPPORT MEMBER FOR USE WITH AN ORTHOPEDIC DEVICE

This application is a continuation-in-part application of U.S. Ser. No. 903,289, (abandoned) filed Sept. 3, 1986, which is hereby incorporated by reference.

BACKGROUND OF THE INVENTION

1. Field of the Invention

The present invention relates to an integral elastic supporting member for use with an orthopedic device. More specifically, the invention discloses an integral flexible elastic support member which is supported from the waist of the user in such a manner that it yields or moves easily in accordance with the movements of the hip joint and the lower limb and the orthopedic device.

2. Description of Prior Art

Some art of interest includes the following:

In U.S. Pat. No. 1,285,507, S. H. Waterman discloses a means for securing an artificial leg which includes a thigh portion contoured to the body of the wearer which includes a belt extending across the back at the waist and uses straps to extend downwardly which are mechanically secured to the artificial leg.

In U.S. Pat. No. 1,858,974, J. A. Swain discloses an attachment by which an artifical leg can be supported from the body of the user which includes a belt which is worn about the waist and having only two straps. One strap loops vertically over or through a loop on the artifical leg. A second strap is connected through a second loop on the artifical leg and connected to the belt on the opposite side of the wearer. In this way, two straps in the front cross each other, and two straps in the back cross each other insuring relatively unrestricted movement of the hip joint and artifical leg.

In U.S. Pat. No. 2,381,265, S. J. Dew discloses a flexible support for an artifical leg. The device includes a belt encircling the waist of the wearer, a series of pulleys anchored to the encircling belt, and pulleys on the artificial leg, all connected by an endless rope or belt. This flexible connector acts to hold the artifical leg on the stump of the wearer and is free to shift around the pulleys responsive to any motion of the wearer.

A general discussion of artifical limb suspension systems is also found in the *Atlas of Limb Prosthetics (Surgical and Prosthetic Principles)*, published by the C. V. Mosby Company of St. Louis, Mo. in 1981.

None of the above references individually or in combination disclose or suggest the present invention.

It is therefore useful and desirable as an object of the present invention to have an integral flexible elastic support member for an orthopedic device which has flexible characteristics responsive to any motion or movement imparted to the orthopedic device.

It is another object of this invention to provide an integral flexible elastic support for an orthopedic device which has a V-shaped adductor panel on the surface of the support member on the side of body which has the orthopedic device.

It is another object of this invention to provide an integral flexible elastic support for an orthopedic device which has a panel opening (or fenestration) within the adductor panel on the side of the body which has the orthopedic device.

Is is yet another object of this invention to provide a flexible elastic support member for use in combination with an artificial leg which has flexible characteristics responsive to any motion or movement imparted to the artifical leg.

It is still another object of this invention to provide flexible elastic support member for use with a fracture cast or orthosis on a human leg which has flexible characteristics responsive to motion imparted to the cast or orthosis.

SUMMARY OF THE INVENTION

The present invention relates an elastic support member for holding an orthopedic device on the leg, such as a fracture casts, orthosis or an artifical leg securely on the lower residual limb of a human body having an above the knee amputation of a leg. The member includes:

an elongated flexible elastic belt portion having free ends, for encircling the lower torso of a human body, attachment means attached at said free ends for detachably connecting said free ends together, and at least one flexible sleeve formed integrally with said belt portion and extending downwardly therefrom to grip and provide support for the orthopedic device.

DETAILED DESCRIPTION OF THIS INVENTION AND PREFERRED EMBODIMENTS

As used herein:

"Cast" refers to a plaster cast, fiber cast, polymeric cast or combination thereof generally used in the treatment of healing or correcting of damaged, fractured, or diseased bone structure. It may also be used to assist in healing of tissue.

"Orthopedic device" or "orthosis" refers to a device, appliance or apparatus used to support, align, prevent, correct deformities, or to improve the function of the movable parts of the body. It may include prosthetic devices, oethotic devices and the like.

"Orthotics" refers to the field of knowledge and use of orthopedic devices.

"Prosthetic device" or "prosthesis" refers to a device, an appliance or apparatus used to replace the function or appearance of a portion of the body which has been removed or amputated. The term may also include a cast on the whole intact leg or a portion thereof.

Prosthetic Device

Figure 1:
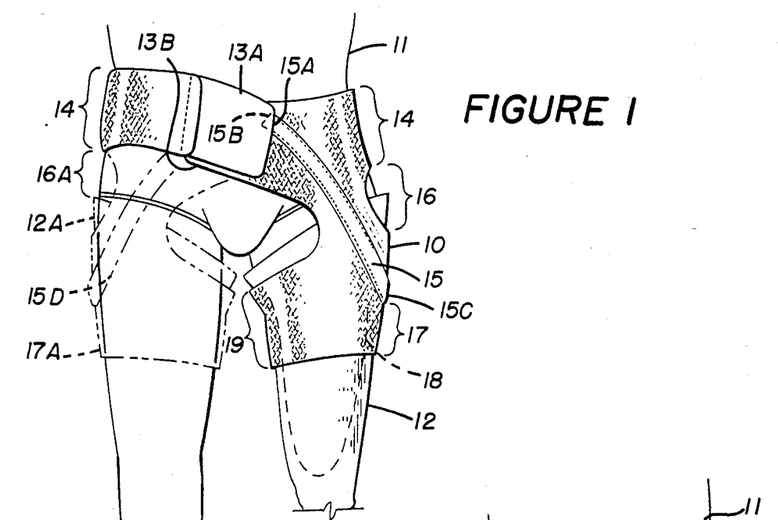
FIG. 1 shows a view of a human having an above the knee amputation of the left leg wherein the human is fitted with an artifical leg using the flexible support member of the present invention.
Figures 2, 3:
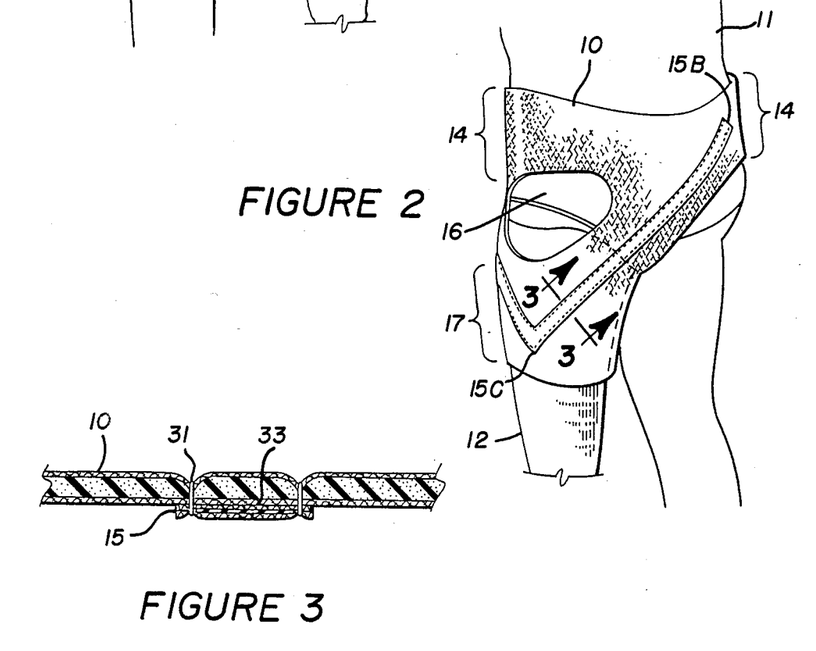
FIG. 2 shows a rear quarter view of a human wearing the member.
FIG. 3 shows a cross-sectional view of the flexible support member at Line 3—3 of FIG. 2.

Referring now to FIGS. 1 and 2 a human being 11 is shown in front view and rear quarter view wearing in place the elastic support member 10 (see also FIG. 4) of the present invention in conjunction with an orthopedic device, such as a prosthesis, e.g., artificial leg 12. Attachment means 13A and 13B are shown connected in the front at the ends of the contoured waist belt or area 14. This most general embodiment of the elastic supporting member does not require either additional panels for support or one or more openings to provide additional flexibility. Optionally, a V-shaped panel and/or an opening generally within the V of the panel provide additional features. The V-shaped adductor panel 15 is shown having an anterior end 15A at the front, a posterior end 15B at the back near the spine and a lower point 15C. Those views also show the interadductor panel opening (fenestration) 16, a socket interfacing cuff 18 [and lower residual limb 18 in dashed outline (- - - -)].

The elastic support member 10 is primarily intended for use by individuals having above the knee amputation in order to suspend or assist in the suspension of an artificial leg 12. Its usefulness and appropriateness is especially apparent in providing a level of comfort and security that relates directly to the maintenance and enhancement of daily activities. Member 10 can be considered a primary suspensor in the absence of atmospheric suspension (AS) or as auxiliary in conjunction with AS. in its role as primary suspensor, it is intended to serve the needs of those with low endurance to presently exhaustive or uncomfortable suspension methods, or to those who are experiencing significant soft tissue changes at their residual limb and require an interim suspension method until stability is achieved. As an auxilliary suspensor, member 10 serves the needs of those with moderate to high endurance levels who can utilize AS to some degree and require additional suspension in the presence of high levels of perspiration or intra-socket muscular activity. In summary, member 10 allows for comfort and security in its application through its unique total elasticity.

The present design allows for intimate conformity to the range of motion found at the hip joint, and the controlled pre-loaded distribution of forces acting to displace artificial leg 12. This conformity provides a degree of comfort not presently found in suspension systems. Under normal conditions, the support member relies completely on its elasticity (at cuff 17) to grasp the artificial leg socket, therefore obviating the usual mechanical fixation points (e.g. rivets, buckles, chafes, loops). When indicated, due to insufficient surface area of the above knee (as in AK) socket or other conditions leading to inadequacy of the grasp between the cuff (at 17) and the AK socket, VELCRO ® may be added at selected locations to the interior surface of the cuff and exterior surface of the AK socket. In need, this will provide additional security against vertical and transverse displacement. Different elastic fabrics and materials may be combined to achieve the desired elasticity.

The elastic fabric or fabric composite must not be too rigid so that it is not flexible or conformable to the body or not provide the necessary support for the artificial leg. On the other hand the fabric must not be too elastic so that the proper support is maintained. It appears that an elongation of 25 to 80% of the original fabric size is preferred, and 35 to 75% elongation is especially preferred. A preferred material is between $\frac{1}{2}$ to $\frac{1}{8}$ inch thick neoprene-nylon two-side material sold as (N2S) by Rubatex Company of Sausalito, Calif. Especially preferred is flexible material between $\frac{1}{8}$ and $\frac{1}{4}$ inch in thickness.

Elastic waist belt portion 14 is designed to fit either in the inter-iliotrochanteric region of the torso or just above the iliac crest on the affected side and wrap circumferentially around the body to a comfortable position and terminates in front having the free ends with 13A and 13B attachment means attached to the free ends.

The supporting member (device) described herein is easily removed from the body, comprised of materials which may be washed repeatedly, allows for normal excretion with a minimum of inconvenience, and provides sufficient grasp of the artificial leg through elastic cuff tension.

The supporting device can be easily modified through incorporation of a second cuff to be applicable to those humans who have lost both legs above the knee. This is shown in different dashed outline (- - - - - - - - - - - - -) in FIG. 1 as second cuff 17A and artificial leg 12A. This embodiment optionally has an adductor panel 15 D and/or opening 16 A.

The contoured waist belt portion 14 may be connected by any means (e.g., a buckle and strap, lace and eyelets and the like) useful to provide the proper support. Particularly preferred are detachable fastening means generally known inthe art as a VELCRO ® fasteners, which are easily adjustible. The VELCRO ® fastening means are basically multiple flexible hooks on one portion and multiple loops on the other portion as is described in U.S. Pat. No. 2,717,434, which is incorporated herein by reference. A preferred waist belt portion comprises about a 3 to 5 inch wide belt of an elastic fabric or fabric composite.

A preferred fabric facing on the waist belt is VELCRO compatible as is manufactured by Rubatex under the terminology "unbroken loop." This fabric has multidirectional stretch similar to the rubber to which it is bonded. By using VELCRO hook in the location of FIG. 8, 13B, the waist belt is adjustable by affixing the hook along any surface portion of the waist belt.

The closure means can be designed with multiple cut-off lines on the tail side of the belt to allow adjustable modification to the desired firth while maintaining a finished edge. The other elements of the elastic member suspend from the belt and control the prosthesis.

Cuff 17 consists of a sized substantially cylindrical-like shape which suspends downwardly from belt 14 and below panel 15. It is designed to encompass about one-third of the proximal end and area of the prosthetic socket. This area is grasped with sufficient force to support the total weight of the artificial leg, and to hold the artifical leg securely to the lower residual limb. Support is provided against both vertical and transverse displacement during normal use. Optionally, VELCRO ® may provide additional support. In a preferred embodiment the cuff comprises a small, medium or large sized cylinder of between about $\frac{1}{8}$ to $\frac{1}{2}$ inch thick Neoprene-nylon fabric composite (nylon fabric one one-side or both sides of the Neoprene—sold as N1S or N2S, respectively). Especially preferred is fabric from about $\frac{1}{8}$ to $\frac{1}{4}$ inch thick.

Figure 4:
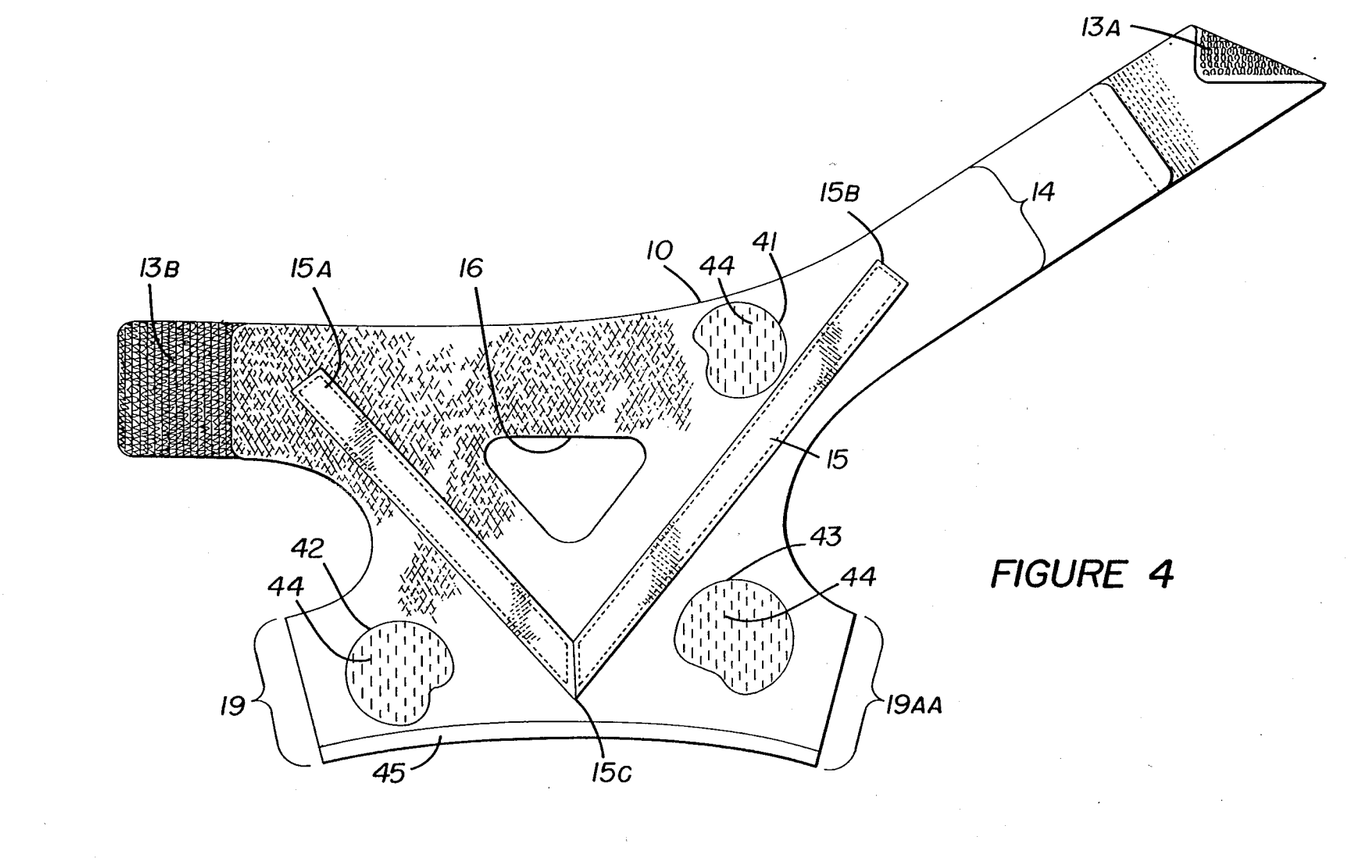
FIG. 4 shows an exterior view of total elastic support member opened for a full view.

The V-shaped adductor panel 15 may be located on the exterior, interior or both sides of the elastic member, as shown in FIG. 1 and FIG. 4. In a preferred embodiment a small, medium or large piece of the Neoprene-nylon (N1S or N2S) is located in external lateral surface of the supporting device. Point 15C is fixed to the distal lateral surface socket interfacing cuff having two portions running in upward directions. The anterior portion terminates at end 15A near attachment means 13B of waist belt 14. The anterior portion terminates at end 15B approximately midline (near the spline of the wearer) on the waist belt as shown in FIG. 2. Panel 15 is affixed around its entire surface and border by sewing (thread 31), gluing (33) or the like to become an integral part of support device 10. Adductor panel 15 is generally between 0.5 and 3 inches wide, between 1/16 and ⅜ inches thick and may be formed of the same material as the overall member 10. Less elastic materials are also useful (e.g. elastic webbing and the like). A preferred elastic webbing (1 inch wide and ⅛ inch thick) is available from J. P. Stevens and Co., United Elastic Division, Stuart, Va. 24171, having about a 50% elongation.

Adductor panel 15 assists the adductor muscle group in the positioning of support device 10 in the appropriate orientation and also provides a zone for the transfer of forces between interfacing cuff 17 and waist belt 14 necessary to control and suspend artificial leg 12.

The inter-adductor panel opening 16 may be of any general shape, generally within V-shaped panel 15. In a preferred embodiment, opening 16 is generally triangular having sides of roughly equal length. One point is generally pointed downward with the two sides bordering V-shaped panel 15. The top side generally parallels the top of waist belt 14. Generally, there is between 1–3 inches of elastic fabric between adductor panel 15 and opening 16, and 3 to 8 inches between the top of the belt and the top side of opening 16. Opening 16 allows for greater independent motion of the anterior and posterior portions of adductor panel 15. It also provides adjustment of the lateral waist belt to be comfortable and support in positions and decreases the bulk and constrictive nature common with presently available prosthetic suspension device systems. The opening 16 also serves to provide ventilation for the body area covered by member 10.

The overall elastic support device is most conveniently manufactured from a flat blank of flexible material cut generally as shown in FIG. 4 (exterior view of member 10 of FIG. 1 opened up). The attachment means 13A and 13B (VELCRO fasteners) are sewn and/or glued to the ends of the belt portion 14, and panel 15 is sewn and/or glued on. Panel 15 may be on the interior side, the exterior side, or both sides of device 10.

Generally, the substantially cylindrical cuff 17 (sleeve) is formed by sewing and/or gluing a seam combining edges 19 and 19AA. In the embodiment having two cuffs (17 and 17A of FIG. 1), the blank is formed in a similar manner.

Additional small openings optionally may be made in member 10 for ventilation. In one embodiment as shown in FIG. 4, Areas 41, 42 or 43 openings 44 are single substantially vertical small cuts through the entire thickness of the fabric. In this pattern of cuts, elastic strength is generally retained, but when the elastic fabric is stretched small openings appear (less than ¼ inch in width) that provide for extra ventilation.

Finally, in the event that the elastic Cuff 17 is found to need additional reinforcement, it is contemplated that member 10 additionally include an elastic reinforcment cuff at the lower end of Cuff 17. The reinforcement Cuff 45 (in FIG. 4) about 0.5 to 6, preferably 2 to 5, inches in width is usually made of the same flexible material as member 10, however, it is possible to use a different elastic or non-elastic material. such as nis textured skin or a non-elastic, adjustable, dacron band.

The support member may be formed, in addition to average adjustable sizes, in small sizes for infants and small children, and in large sizes for very large or obese adults.

Orthopedic Device

The description herein is generally to a support member for use in medical applications with human beings. It is apparent to one of skill in this art that the support member is also useful in applications where an amputation of the human leg has not occurred, but one in which the leg has been injured. In other words, the support member is useful to assist in the suspension of an orthopedic device, such as an orthotic device or a plaster or fabric cast used in the treatment of a human leg which has been broken, or fractured, or is diseased. In the description and the claims herein, if the term "prosthesis device" or "artifical leg" is read as "an orthopedic device", "orthotic device" or "a leg cast" and the term "having at least one above the knee amputation" is read as having at least one orthopedic device, orthotic device or fracture cast—. The size of the elastic support member to be used is selected by the physician surgeon or other appropriate medical professional to provide the desired support and flexibility for the individual patient having the affected lower extremity.

Figures 5, 6:
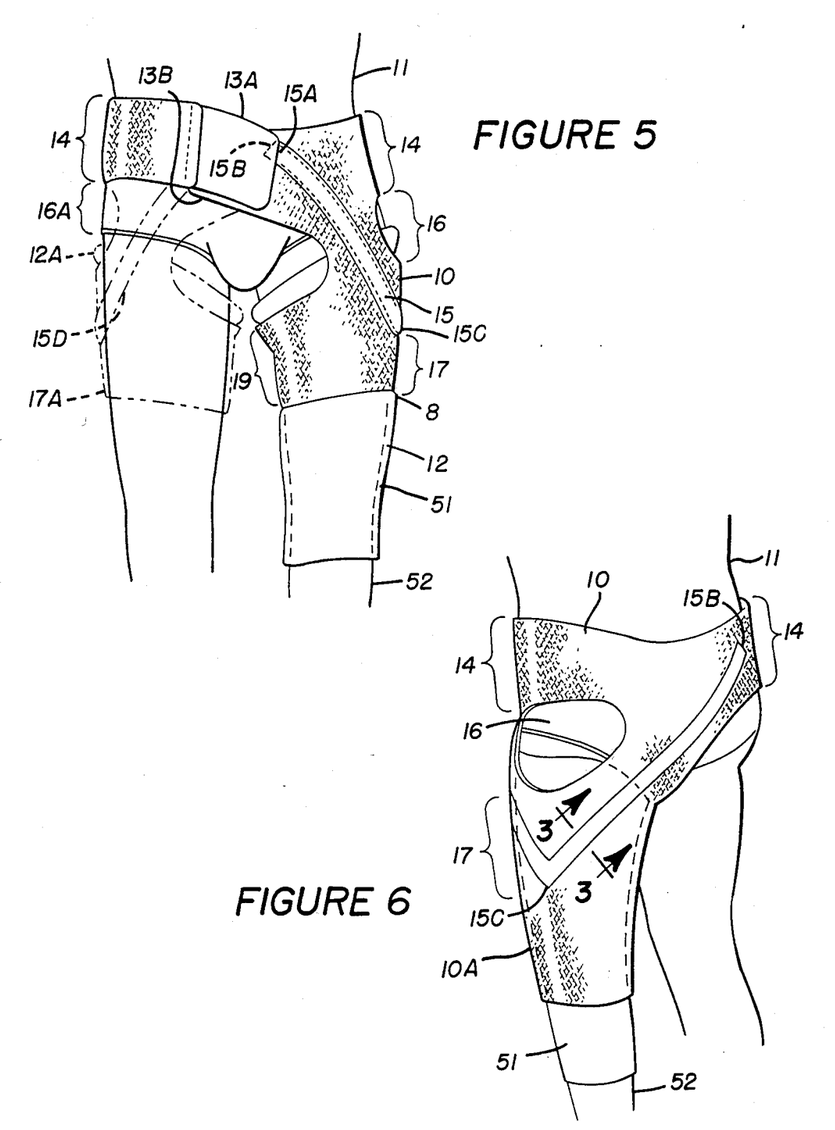
FIG. 5 shows a front view of a human being having a plaster cast on the thigh and knee portion of the leg and the flexible support member.
FIG. 6 shows a rear quarter view of a human having the plaster cast wearing the support member.

As shown in FIG. 5 and FIG. 6 is a human having an orthopedic device being supported by the flexible member of this invention. Where the numbers are the same, they have the same meaning as described in FIG. 1, 2, 3 and 4 above. In FIG. 5, the plaster fracture cast 51 on injured leg 52 is supported by member 10. The member fits snugly around the cast and provides the additional support to enable the patient to move about in a more normal manner.

FIG. 6 shows a rear quarter view of the member and cast of FIG. 5. In this Figure sleeve 10A is much longer to provide additional support for cast 51 on injured leg 52.

In most broad applications the support member where the sleeve is just sewn together will be satisfactory. In some applications a custom-made support member may need to be produced. In this way the sleeve will slip up over the orthopedic device (Cast or prosthesis) and provide for the support.

Figure 7:
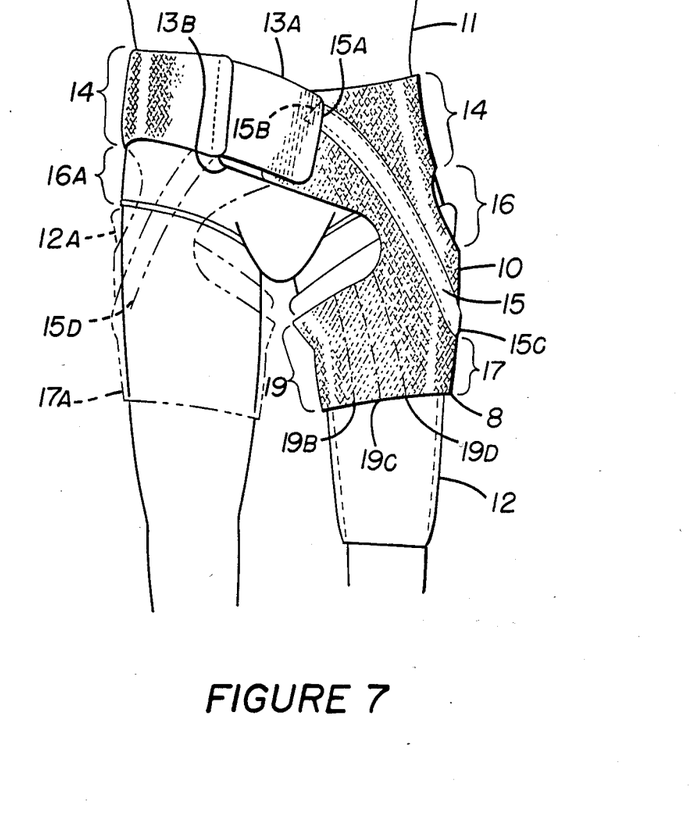
FIG. 7 shows a front view of a human having a plaster cast on the thigh and knee portion of the leg and the flexible support member which is detachable at the sleeve to adjust about and encircle about the cast.
Figure 8:
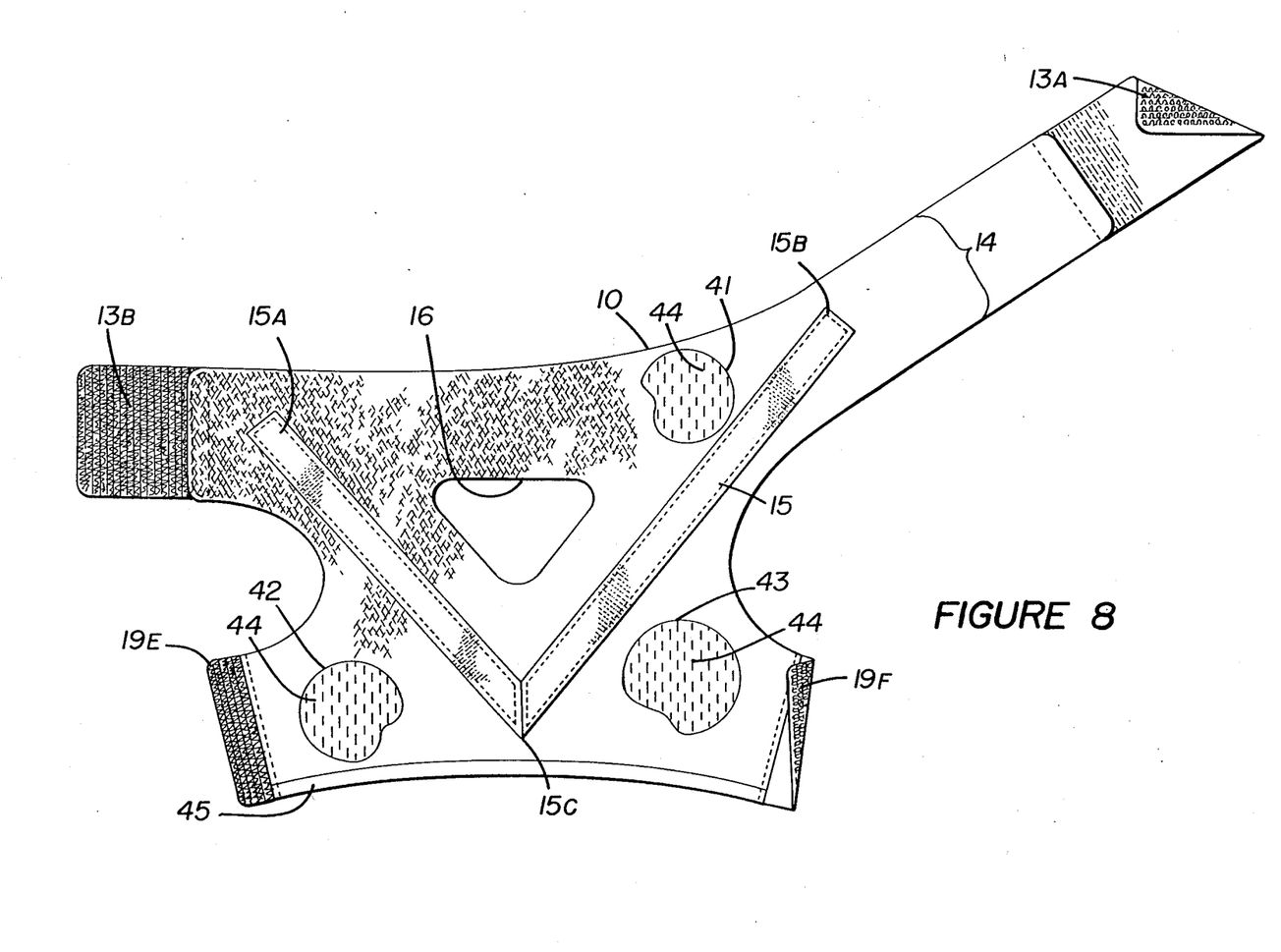
FIG. 8 shows an exterior planar view of the support member of FIG. 7 having the detachable fastening means on the sleeve.

In other instances, it may be necessary to have the sleeve constructed so that it is reversibly detachable at the lower portion of the sleeve. The vertical detachable area (second detachable attachment means) may be at any location on the sleeve as shown in FIG. 7 (lines 19B, 19C or 19D); however, it is preferably found at seam 19(19AA) for convenience. As shown in FIG. 8 in one embodiment (at the seam numbered 19 (19AA) of FIG. 4), VELCRO ® hook and loop fasteners 19E and 19F are sewn or adhered to the support member. When 19E and 19F are adjustably attached to each other, the sleeve formed will support the orthopedic device. If other or additional attachment means are needed, eg. belt and loop, etc., on the sleeve portion, they may be employed within the scope of this invention.

While some embodiments of the invention have been shown and described herein, it will become apparent to those skilled in the art that various modifications and changes can be made without departing from the spirit and scope of the present invention. All such modifications and changes coming within the scope of the appended claims are intended to be covered thereby.

We claim:

1. An integral elastic support member adapted for encircling the human body for holding an orthopedic device securely on the leg or a prosthetic device on the lower residual limb of a human body having an above the knee amputation of a leg, which member comprises:
   an elongated flexible elastic belt portion having free ends for encircling the lower torso of a human body,
   attachment means for detachably connecting said free ends together, and
   at least one flexible elastic sleeve means formed integrally with said belt and extending downwardly therefrom to encircle and to grip the top outer surface of the orthopedic device and provide flexible support for the orthopedic device, and
   a V-shaped adductor panel attached to the surface of the member positioned so that, when the member is worn, the adductor panel has the apex point generally directed in a downward direction attached to the lower sleeve means, with the sides pointing at generally about a 45° angle to the horizontal extending upwardly and attached to the belt portion, wherein the integral elastic support member comprises an elastic material having an elongation of 20 to 80% of the unstretched material.

2. The member of claim 1 wherein said attachment means are VELCRO® hook and loop attachment means.

3. The member of claim 2 wherein said member is formed of a flexible neoprene rubber.

4. The member of claim 1 which additionally includes a panel opening in the supporting member, which when the supporting member is worn, the opening is on the outer side of the human body which has the orthopedic device.

5. The member of claim 4 which additionally includes a panel opening generally found within said adductor band in the supporting member, which when the supporting member is worn, the opening is on the outer side of the human body which has the orthopedic device.

6. The member of claim 5 wherein said attachment means are VELCRO® flexible multiple hook and loop attachment means.

7. The member of claim 6 wherein said member is formed of a flexible neoprene rubber.

8. The elastic support member of claim 1 wherein the orthopedic device is a leg cast.

9. The member of claim 1 wherein the sleeve is formed by connecting second detachable attachment means.

10. The integral elastic support member of claim 1 wherein the prosthetic device is an artificial leg.

11. The member of claim 10 wherein said attachment means are VELCRO hook and loop attachment means.

12. The member of claim 11 wherein said member is formed of a flexible neoprene rubber.

13. The elastic support memer of claim 1 wherein the member additionally includes small holes in the fabric of the member to aid in dissipation of heat from the human.

14. The member of claim 1 wherein the bottom of the sleeve has an additional reinforcing elastic cuff.

15. The elastic support member of claim 1 wherein the sleeve is formed by connecting second detachable attachment means and the orthopedic device is a leg cast.

16. The elastic support member of claim 15 wherein the second detachable attachment means are VELCRO hook and loop attachment means.

17. The elastic support member of claim 1 wherein the sleeve is formed by a second detachable attachment means and the prosthetic device is an artificial leg.

18. The elastic support member of claim 17 wherein the second detachable attachment means are VELCRO hook and loop attachment means.

19. An elastic integral flexible support member adapted for encircling the lower torso of a human being for securely supporting an orthopedic device on a leg or a prosthetic device on the residual lower limb of a human being having at least one above the knee amputation, the member comprising
   an adjustable body encircling portion having free ends which have detachable attachment means,
   attachment means for detachably connecting said free ends together;
   at least one flexible substantially cylindrical elastic sleeve means formed integrally with said body encircling portion, the sleeve means descending downwardly from the body encirciling means to encircle and to grip the top outer surface of the orthopedic device and to provide support for at least one orthopedic device and;
   a V-shaped adductor panel attached to the surface of the member and positioned so that, when the member is worn, the panel has the apex point generally directed in a downward direction attached in the lower region of the sleeve meas, with the sides extending upwardly and attached to the surface of the front and back of the belt portion on the outer side of the body which has the orthopedic device.

20. The member of claim 19 wherein said attachment means are VELCRO ™ flexible multiple hook and loop means, and the flexible member comprises a neoprene fabric.

21. The member of claim 19 wherein said member additionally includes small holes in the fabric of the member to aid in dissipation of heat from the human.

22. The member of claim 19 wherein the bottom of the sleeve had an additional reinforcing elastic cuff.

23. The member of claim 19 wherein the sleeve is formed by connecting second detachable attachment means.

24. The member of claim 23 wherein the second detachable attachment means comprise VELCRO® multiple flexible hook and loop attachment means.

25. The elastic integral flexible support member of claim 19 wherein the prosthetic device is an artificial leg.

26. The member of claim 25 wherein said attachment means are VELCRO hook and loop attachment means.

27. The member of claim 26 wherein said member is formed of a flexible neoprene rubber.

28. The elastic support member of claim 19 wherein the sleeve is formed by second detachable attachment means and the prosthetic device is an artificial leg.

29. The elastic support member of claim 19 wherein the sleeve is formed by connecting second detachable attachment means, and the orthopedic device is a leg cast.

30. The elastic support member of claim 29 wherein the second detachable attachment means are VELCRO hook and loop means.

31. The member of claim 19 which additionally includes a panel opening in the member, which when the member is worn, the opening is on the outer side of the body which has the orthopedic device.

32. The member of claim 31 where said attachment means are VELCRO® hook and loop attachment means, and the flexible member comprises a neoprene fabric.

33. A blank comprising a flexible elastic material useful in the production of a flexible elastic supporting member for supporting an orthopedic device on a leg or prosthetic device securely on the lower residual limb of a human being having an above the knee amputation of at least one leg, which blank includes:
- an elongated flexible elastic belt portion having free ends for encircling the lower torso of a human body,
- attachment means connected at said free ends for detachably connecting said free ends together,
- at least one flexible elastic portion descending downwardly from the body encircling means which when connected upon itself creates flexible elastic substantially cylindrical elastic sleeve means which is formed integrally with said body encircling portion, and
- a V-shaped adductor panel attached to the surface of the blank and positioned so that when the blank is formed into an elastic support member, the panel has an apex point of the V generally directed in a downward direction and attached in the outer lower portion of the sleeve means, with each side of the V pointing outwardly at generally about a 45° angle to the horizontal and attached to the belt portion, wherein the point of the V is generally positioned about the middle of the side of the human which has an orthopedic device.

34. The blank of claim 19 wherein the sleeve is formed by second detachable attachment means.

35. The blank of claim 34 wherein the second detachable attachment means are VELCRO hook and eye means.

36. The blank of claim 33 where the prosthetic device is an artificial leg.

37. The blank of claim 36 wherein the blank has attachment means of VELCRO hook and loop attachment means.

38. The blank of claim 37 wherein the blank is formed of a flexible neoprene rubber.

39. The elastic support member of claim 33 wherein the orthopedic device is a leg cast.

40. The blank of claim 33 which additionally includes a panel opening in the blank which is generally within the V-shaped adductor panel.

41. The blank of claim 40 wherein the flexible elastic material is neoprene/nylon composite material, and the attachment means are VELCRO® hook and loop attachment means.

42. The elastic support member of claim 19 wherein the orthopedic device is a leg cast.

* * * * *